(12) United States Patent
Casteel, Jr. et al.

(10) Patent No.: US 6,307,105 B1
(45) Date of Patent: Oct. 23, 2001

(54) HIGH PURITY PREPARATION OF FLUORINATED 1,3-DICARBONYLS USING BDM (BIS-FLUROXY DIFLUOROMETHANE)

(75) Inventors: William Jack Casteel, Jr., Emmaus; Robert George Syvret, Allentown; Wade Hampton Bailey, III, Emmaus, all of PA (US)

(73) Assignee: Air Products and Chemicals, Inc., Allentown, PA (US)

( * ) Notice: Subject to any disclaimer, the term of this patent is extended or adjusted under 35 U.S.C. 154(b) by 0 days.

(21) Appl. No.: 09/619,604

(22) Filed: Jul. 19, 2000

(51) Int. Cl.$^7$ .................................................. C07C 45/63
(52) U.S. Cl. ........................ 568/393; 570/201; 570/203
(58) Field of Search ............................ 568/393; 570/201, 570/203

(56) References Cited

U.S. PATENT DOCUMENTS

| 4,766,243 | 8/1988 | Fifolt ..................... 564/414 |
| 5,391,811 | 2/1995 | Bohm et al. .............. 560/43 |
| 5,569,778 | 10/1996 | Umemoto et al. ........... 560/121 |

FOREIGN PATENT DOCUMENTS

| 0891962 | 1/1999 | (EP) . |

OTHER PUBLICATIONS

Fifolt, et al., "Fluorination of Aromatic Derivatives with Fluoroxytrifluoromethane and Bis(fluoroxy)difluoromethane," J. Org. Chem. 1985, 50(23), 4576.

Patrick, "Electrophillic Fluorination of Carbon–Hydrogen Bonds," Chemistry of Organic Fluorine Compounds II 1995, 133.

Stavber, et al., "Room–temperature Reactions of ScSO$_4$F with Organic Molecules Containing Heteroatoms," J. Chem. Soc., Chem. Comm., 1983, 563.

U.S. Patent Application No. 09/432,723, Entitled "Direct Fluorination Process for Preparing High Purity 2–Fluoro–1, 3–Dicarbonyl Compounds Using Oxygen as a Radical Scavenger" Filed Nov. 1, 1999 (Pending).

Primary Examiner—Johann Richter
Assistant Examiner—Sikarl A. Witherspoon
(74) Attorney, Agent, or Firm—Geoffrey L. Chase

(57) ABSTRACT

A process for providing an α-fluorinated-β-dicarbonyl includes electrophilically fluorinating a β-dicarbonyl with bis-fluoroxydifluoromethane in the presence of an acid to provide the α-monofluorinated-β-dicarbonyl. The acid is preferably hydrofluoric acid. Preferred β-dicarbonyls include methyl-3-oxopentanoate and ethyl-4,4,4-trifluoroacetoacetate. The process can limit radical impurity byproducts to no more than 4% in some cases, and less than 0.5% in other cases. Theoretical yields of 95% α-monofluorinated-β-dicarbonyl are possible in some cases.

19 Claims, No Drawings

HIGH PURITY PREPARATION OF FLUORINATED 1,3-DICARBONYLS USING BDM (BIS-FLUROXY DIFLUOROMETHANE)

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

This invention relates to processes for electrophilically fluorinating β-dicarbonyls to form the corresponding α-fluorinated-β-dicarbonyls, with the use of bis-fluoroxydifluoromethane (BDM) in the presence of an acid.

Although bis-fluoroxydifluoromethane ($CF_2(OF)_2$), and to a much greater extent the monofluoroxy compound, fluoroxytrifluoromethane ($CF_3OF$), have been used to carry out a number of electrophilic fluorinations (see, e.g., U.S. Pat. No. 4,766243 and Fifolt et al., "Fluorination of Aromatic Derivatives with Fluoroxytrifluoromethane and Bis(fluoroxy)difluoromethane," J. Org. Chem. 1985, 50(23), 4576), the inventors are not aware of any prior art teaching their use for the fluorination of 1,3-dicarbonyls.

On the other hand, there is evidence in the art suggesting that O—F bond-containing compounds are not particularly effective for fluorinating 1,3-dicarbonyls. For example, the use of acetyl hypofluorite, another O—F bond containing compound, has been used successfully in the fluorination of enolate salts of ketoesters, but has proven to be less effective in the fluorination of neutral ketoesters. See, e.g., Patrick, "Electrophillic Fluorination of Carbon-Hydrogen Bonds," Chemistry of Organic Fluorine Compounds II 1995, 133. Similarly, cesium fluoroxysulfate ($CsSO_3(OF)$) gave only a 44% yield of the desired monofluorinated product and 19% of the difluorinated product on reaction with relatively nucleophilic 2,4-pentanedione. See, e.g., Stavber et al., "Room-temperature Reactions of $CsSO_4F$ with Organic Molecules containing Heteroatoms," J. Chem. Soc., Chem. Comm., 1983, 563.

Previously, 1,3-dicarbonyls, such as β-diketones and β-ketoesters, having the formula:

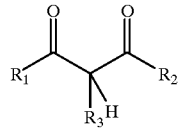

Formula 1 where $R_1$ is H, alkyl or alkoxy, $R_2$ is H, alkyl or perfluoroalkyl, and $R_3$ is H, Cl, Br, I or alkyl, have been fluorinated directly with fluorine in acidic solvents or in polar solvents containing acidic, or weakly basic, polar additives. While this methodology has been reasonably selective, the desired monofluorination products still contain 10–35% radical fluorination impurities (the term "radical fluorination impurities" refers to products resulting from fluorination at $R_1$ and/or $R_2$ in Formula I above) at substrate loadings of only 5–10 wt. % in the chosen solvent. See, e.g., U.S. Pat. No. 5,569,778 (Umemoto et al.)

Another technique for fluorinating the alpha carbon in β-dicarbonyls comprises directly fluorinating β-dicarbonyl compounds with fluorine in a reactive medium comprising a radical scavenger, such as oxygen, that inhibits side reactions between fluorine and acid additives. See the inventors' prior U.S. patent application Ser. No. 09/432,723, filed Nov. 1, 1999.

EP 0891962 (Nukui et al.) discloses a process for preparing fluorinated dicarbonyl compounds comprising reacting dicarbonyl compounds and fluorine gas without any solvent and in the presence of at least one acid selected from the group consisting of trifluoromethanesulfonic acid (i.e., triflic acid), methanesulfonic acid, hydrofluoric acid, sulfuric acid, trifluoroacetic acid, boron trifluoride and sulfonated polymers. Nukui et al. discloses that the substrate loadings have been substantially increased in very strong acids (up to 88 wt. % methyl-3-oxopentanoate (MOP) in highly acidic triflic acid), but gives only 16 wt. % fluorination impurities, including 2,2-difluorinated impurity. However, these fluorinated impurities are often difficult to separate from the desired product and many of them are carried forward in subsequent reaction steps.

Additionally, higher purity fluorinated dicarbonyls have been obtained by a number of multistep methods. For example, the dicarbonyl compound has been converted, using a strong base, into its enolate salt which has been fluorinated by a more selective, but costly, electrophilic fluorinating reagent. By this method, the dicarbonyl compound has been chlorinated and then fluorinated by halogen exchange. This method gives only moderate yields (30–80%) of fluorinated product, which must still be purified by fractional distillation. See, e.g., U.S. Pat. No. 5,391,811 (Böhm et al).

Despite the foregoing developments, there is still room in the art for improved fluorination methods.

All references cited herein are incorporated herein by reference in their entireties.

BRIEF SUMMARY OF THE INVENTION

The invention comprises a process for providing an α-fluorinated-β-dicarbonyl, said process comprising electrophilically fluorinating a β-dicarbonyl with bis-fluoroxydifluoromethane in the presence of an acid to provide said α-fluorinated-β-dicarbonyl.

BRIEF DESCRIPTION OF SEVERAL VIEWS OF THE DRAWINGS

Not applicable.

DETAILED DESCRIPTION OF THE INVENTION

A preferred process of the invention comprises electrophilically substituting a single fluorine group on the alpha-carbon of a β-dicarbonyl by reacting the β-dicarbonyl with bis-fluoroxydifluoromethane (BDM) in the presence of an acid, as shown in Equation I:

Equation 1

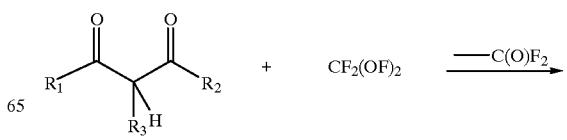

-continued

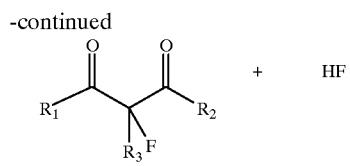 + HF where $R_1$ is H, alkyl or alkoxy, $R_2$ is H, alkyl or perfluoroalkyl, and $R_3$ is H, Cl, Br, I or alkyl. The products of the inventive process (e.g., α-monofluorinated-β-dicarbonyls, such as methyl-2-fluoro-3-oxopentanoate) are important precursors to fluorinated heterocycles used in the pharmaceutical industry.

Conventional processes of direct fluorination typically provide fluorinated carbonyl products which are only 75–85% pure and contaminated with radical fluorination byproducts, which are difficult to separate. On the other hand, the instant invention, comprising the use of bis-fluoroxydifluoromethane, provides selectivity (for the α-monofluorinated-β-dicarbonyl product) in an amount from about 88 to about 96% in the fluorination of the neat β-dicarbonyl compound to which small amounts of acid have been added. The selectivity is even greater for embodiments of the invention comprising fluorinating a 10–25 wt. % solution of the substrate in an acid. Such embodiments provide selectivity from about 95% to 100% preferably, about 99% to 100%, more preferably about 99.5 to 100%. Thus, preferred embodiments of the invention limit the amount of radical fluorination impurities to less than 12%, more preferably 4% or less, and even more preferably less than 0.5%.

β-dicarbonyl substrates suitable for use in the invention include, e.g., methyl-3-oxopentanoate, ethyl-4,4,4-trifluoroacetoacetate, 2,4-pentanedione and other diketones and ketoesters of the form shown in Formula I and Equation I, above. Accordingly, typical products of the invention include, e.g., methyl-2-fluoro-3-oxopentanoate, ethyl-2,4,4,4-tetrafluoroacetoacetate, 3-fluoro-2,4-pentanedione and other α-fluoro-β-dicarbonyls of the form shown in Equation I, above.

Hydrofluoric acid (HF) is the preferred acid catalyst of the invention, but other suitable acid catalysts include, e.g., triflic, fluorosulfonic, sulfuric, formic, acetic and trifluoroacetic acids, and Lewis acids such as $BF_3$.

In embodiments of the inventive process, BDM is produced in a flow system from $F_2$ and $CO_2$. In these and other embodiments of the invention, BDM and any additional components, such as $F_2$, are preferably charged into a reactor (e.g., an FEP reactor) in an inert carrier, such as nitrogen, $CO_2$, dry air, Ar, He, etc. The ratio (volume:volume) of BDM to inert carrier is preferably about 0.5:99.5 to about 10:90, preferably 3:97 to 5:95. Ratios outside these ranges are either impractical or hard to control because of reaction exothermicity.

It is preferred to add about 1 to 1.5, preferably 1 to 1.2 equivalents of electrophile (e.g., BDM or BDM/$F_2$) to the substrate. Adding more than 1.5 equivalents is inefficient and/or promotes undesirable side reactions. Adding less than 1 equivalent leaves a portion of the substrate unreacted.

In embodiments where BDM and $F_2$ are used as electrophiles, the ratio (in equivalents) of BDM to $F_2$ is preferably from 5:6 to about 6:5, more preferably from 9:8 to 6:5.

In embodiments, BDM is directly delivered into a reactor containing: (a) a 5 to 85 wt. %, preferably 10 to-25 wt. % solution of the dicarbonyl substrate in strong acid; (b) a 5 to 30 wt. %, preferably 10–25 wt. % solution of the dicarbonyl substrate in a mixture of a strong acid and methanol (preferably containing 33 to 50 wt. % strong acid and 67 to 50 wt. % methanol); or (c) the neat substrate containing 5 to 30 wt. %, preferably 10–20 wt. % acid additive. In certain embodiments using a strong acid solution, less than 1% radical fluorination impurities are observed. Radical fluorination impurities increase if the acid solvent is diluted with methanol, and at higher levels of methanol dilution, the substrate becomes deactivated towards fluorination. When BDM is used in the fluorination of the substrate without solvent (i.e., when neat substrate is used), in the presence of a small amount of added acid, only small amounts of fluorination impurities, including 2,2-difluorinated impurity, are observed. The process, therefore, offers the advantages of comparable cost to direct fluorination, with significantly higher yields and purities obtained at high substrate loadings.

If the dilute BDM stream contains some fluorine, the selectivity of the fluorination is reduced. However, the BDM/$F_2$/$N_2$ mixture still performs better than $F_2$/air or $F_2$/$N_2$ at relatively high substrate loadings. Dilute mixtures of BDM and fluorine are more selective than dilute $F_2$ alone. Thus, for example, a 50 wt. % substrate solution in HF shows only 3 wt. % radical fluorination impurities when fluorinated with a 55:45 mixture of BDM:$F_2$ diluted with $N_2$, compared to 11 wt. % radical fluorination impurities for a 38 wt. % substrate solution fluorinated with $F_2$/air and 14–15 wt. % radical fluorination impurities for a 26 wt. % solution fluorinated with $F_2$/$N_2$.

At high substrate loadings, such as 50 wt. % to about 85 wt. %, the addition of oxygen, by dilution of BDM:$F_2$ mixtures with air, significantly reduces levels of radical fluorination impurities. At 80–85 wt. % loading, the amount of 4-fluoro-methyl-3-oxopentanoate decreases from 23% of the total product to 1.5%, with addition of oxygen to the dilute BDM:$F_2$ fluorination mixture.

The invention will be illustrated in more detail with reference to the following Examples, but it should be understood that the present invention is not deemed to be limited thereto.

EXAMPLES

Example 1

Methyl-3-oxopentanoate was fluorinated in HF using 5% bis-fluoroxydifluoromethane in accordance with the following example.

A 100 mL FEP reactor was charged with 10 mmol of methyl-3-oxopentanoate (about 1.3 g). The reactor was externally cooled to about −35° C. and 12 mL anhydrous HF were condensed under static vacuum. This corresponds to a substrate loading of 10 wt. %. About 1.0 equivalents of BDM were sparged as a 5% BDM/95% $N_2$ vol/vol. stream into the reactor at −20° C. at 225 mL/min, allowing the effluent to pass through a soda-lime scrubber. After addition of BDM, HF solvent was evacuated through a soda-lime scrubber. The reactor was then opened and 30 mL $H_2O$ were added. The mixture was then neutralized with $NaHCO_3$. The product was extracted with ether.

Analysis of the product by $^1H$ and $^{19}F$ NMR showed 83% conversion of methyl-3-oxopentanoate. The isolated product was 82% pure methyl-2-fluoro-3-oxopentanoate. Radical fluorination impurities in the isolated product totaled less than 0.5%.

Example 2

Methyl-3-oxopentanoate was fluorinated in 1:3 HF/$CH_3OH$ using 3% bis-fluoroxydifluoromethane in accordance with the following example.

A 100 mL FEP reactor was charged with 10 g (77 mmol) methyl-3-oxopentanoate and 30 g MeOH. The reactor was externally cooled to about −35° C. and 10 mL anhydrous HF were condensed under static vacuum. This corresponds to a substrate loading of 20 wt. %. About 0.9 equivalent of BDM was sparged as a 3% BDM/97% $N_2$ stream into the reactor at −25° C. at 300 mL/min, allowing the effluent to pass through a soda-lime scrubber. After addition of BDM, HF solvent was evacuated through a soda-lime scrubber. The reactor was then opened and 30 mL $H_2O$ were added. The mixture was then neutralized with $NaHCO_3$. The product was extracted with hexane.

Analysis of the product by $^1H$ and $^{19}F$ NMR showed 80% conversion of methyl-3-oxopentanoate. The isolated product was 72% pure methyl-2-fluoro-3-oxopentanoate. Radical fluorination impurities in the isolated product totaled less than 5%.

Example 3

Methyl-3-oxopentanoate was fluorinated in 1:6 $HF/CH_3OH$ using 3% bis-fluoroxydifluoromethane in accordance with the following comparative example. This example is outside the scope of the invention, due to low HF:MeOH ratio.

A 100 mL FEP reactor was charged with 4 g (30 mmol) methyl-3-oxopentanoate and 30 g MeOH. The reactor was externally cooled to about −35° C. and 5 mL anhydrous HF were condensed under static vacuum. This corresponds to a substrate loading of 10 wt. %. About 1.1 equivalents of BDM were sparged as a 3% BDM/97% $N_2$ stream into the reactor at −25° C. at 300 mL/min, allowing the effluent to pass through a soda-lime scrubber. After addition of BDM, HF solvent was evacuated through a soda-lime scrubber. The reactor was then opened and 30 mL $H_2O$ were added. The mixture was then neutralized with $NaHCO_3$. The product was extracted with hexane.

Analysis of the product by $^1H$ and $^{19}F$ NMR showed 40% conversion of methyl-3-oxopentanoate. The isolated product was 40% pure methyl 2-fluoro-3-oxopentanoate, the balance being precursor. Radical fluorination impurities in the isolated product totaled <1%.

Example 4

Methyl-3-oxopentanoate was fluorinated in HF using 5% bis-fluoroxydifluoromethane in accordance with the following example.

A 100 mL FEP reactor was charged with 6.9g (53 mmol) methyl-3-oxopentanoate. The reactor was externally cooled to about −30° C. and 1.7 mL anhydrous HF were condensed under static vacuum. This corresponds to a substrate loading of 80 wt. %. About 1.1 equivalents of BDM were sparged as a 5% BDM/95% $N_2$ stream into the reactor at −20° C. at 225 mL/min, allowing the effluent to pass through a soda-lime scrubber. After addition of BDM, HF solvent was evacuated through a soda-lime scrubber. The reactor was then opened and 30 mL $H_2O$ were added. The mixture was then neutralized with $NaHCO_3$. The product was extracted with ether.

Analysis of the product by $^1H$ and $^{19}F$ NMR showed 100% conversion of methyl-3-oxopentanoate. The isolated product was 95% pure methyl-2-fluoro-3-oxopentanoate. Radical fluorination impurities in the isolated product totaled 4%.

Example 5

Neat ethyl-4,4,4-trifluoroacetoacetate was fluorinated using 5% bis-fluoroxydifluoromethane in accordance with the following example.

A 100 mL FEP reactor was charged with 6.9 g (53 mmol) ethyl-4,4,4-trifluoroacetoacetate. This corresponds to a substrate loading of 100 wt. %. About 1.0 equivalent of BDM were sparged as a 5% BDM/95% $N_2$ stream into the reactor at −10° C. at 225 mL/min, allowing the effluent to pass through a soda-lime scrubber. The reactor was then opened and 30 mL $H_2O$ were added. The mixture was then neutralized with $NaHCO_3$. The product was extracted with ether.

Analysis of the product by $_1H$ and $^{19}F$ NMR showed 75% conversion of ethyl-4,4,4-trifluoroacetoacetate. The isolated product was 62% pure ethyl-2,4,4,4-tetrafluoroacetoacetate. Radical fluorination impurities in the isolated product totaled 12%.

Example 6

Methyl-3-oxopentanoate (80 wt. %) was fluorinated in HF using $BDM/F_2/N_2$ in accordance with the following example.

A 60 mL FEP reactor was charged with 15.6 g (120 mmol) methyl-3-oxopentanoate. The reactor was externally cooled to about −25° C. and 4 mL anhydrous HF were condensed under static vacuum. This corresponds to a substrate loading of 80 wt. %. About 0.7 equivalent of BDM and 0.6 equivalent of $F_2$ were sparged as a 5% BDM/4% $F_2$/91% $N_2$ stream into the reactor at −25° C. at 225 mL/min, allowing the effluent to pass through a soda-lime scrubber. After addition of $BDM/F_2$, HF solvent was evacuated through a soda-lime scrubber. The reactor was then opened and 30 mL $H_2O$ were added. The mixture was then neutralized with $NaHCO_3$. The product was extracted with ether.

Analysis of the product by $_1H$ and $^{19}F$ NMR showed 100% conversion of methyl-3-oxopentanoate. The isolated product was 68% pure methyl-2-fluoro-3-oxopentanoate. Radical fluorination impurities in the isolated product totaled 30%. The amount of 4-fluoro-methyl-3-oxopentanoate was 23%.

Example 7

Methyl-3-oxopentanoate (50 wt. %) was fluorinated in HF using $BDM/F_{2/N2}$ in accordance with the following example.

A 60 mL FEP reactor was charged with 11.3 g (87.1 mmol) methyl-3-oxopentanoate. The reactor was externally cooled to about −25° C. and 11 mL anhydrous HF were condensed under static vacuum. This corresponds to a substrate loading of 50 wt. %. About 0.6 equivalent of BDM and 0.5 equivalent of $F_2$ were sparged as a 5% BDM/4% $F_2$/91% $N_2$ stream into the reactor at −25° C. at 225 mL/min, allowing the effluent to pass through a soda-lime scrubber. After addition of $BDM/F_2$, HF solvent was evacuated through a soda-lime scrubber. The reactor was then opened and 30 mL $H_2O$ were added. The mixture was then neutralized with $NaHCO_3$. The product was extracted with ether.

Analysis of the product by $_1H$ and $^{19}F$ NMR showed 95% conversion of methyl-3-oxopentanoate. The isolated product was 91% pure methyl-2-fluoro-3-oxopentanoate. Radical fluorination impurities in the isolated product totaled 3%.

Example 8

Methyl-3-oxopentanoate (85 wt. %) was fluorinated in HF using $BDM/F_2$/air in accordance with the following example.

A 60 mL FEP reactor was charged with 15.3 g (118 mmol) methyl-3-oxopentanoate. The reactor was externally cooled to about −25° C. and 3 mL anhydrous HF were condensed under static vacuum. This corresponds to a substrate loading of 85 wt. %. About 0.6 equivalent of BDM and 0.5 equivalent of $F_2$ were sparged as a 5% BDM/4% $F_2$/6%$O_2$/85% $N_2$ stream into the reactor at −25° C. at 225 mL/min, allowing the effluent to pass through a soda-lime scrubber. After addition of BDM/$F_2$, HF solvent was evacuated through a soda-lime scrubber. The reactor was then opened and 30 mL $H_2O$ were added. The mixture was then neutralized with $NaHCO_3$. The product was extracted with ether.

Analysis of the product by $_1H$ and $^{19}F$ NMR showed 91% conversion of methyl-3-oxopentanoate. The isolated product was 81 % pure methyl-2-fluoro-3-oxopentanoate. Radical fluorination impurities in the isolated product totaled 7%. The amount of 4-fluoro-methyl-3-oxopentanoate was 1%.

Example 9

Methyl-3-oxopentanoate (38 wt. %) was fluorinated in HF using $F_2$/$O_2$/$N_2$ in accordance with the following comparative example.

A 100 mL FEP reactor was charged with 25.6 g (197 mmol) methyl-3-oxopentanoate. The reactor was externally cooled to about −50° C. and 42 mL anhydrous HF were condensed under static vacuum. This corresponds to a substrate loading of 38 wt. %. About 1.1 equivalent (217 mmol) of $F_2$ were sparged as a 10% $F_2$/10%$O_2$/80% $N_2$ stream into the reactor at −30° C. at 300 mL/min, allowing the effluent to pass through a soda-lime scrubber. After addition of $F_2$, HF solvent was evacuated through a soda-lime scrubber. The reactor was then opened and 30 mL $H_2O$ were added. The mixture was then neutralized with $NaHCO_3$. The product was extracted with ether.

Analysis of the product by $_1H$ and $^{19}F$ NMR showed 100% conversion of methyl-3-oxopentanoate. The isolated product was 85% pure methyl-2-fluoro-3-oxopentanoate. Radical fluorination impurities in the isolated product totaled 11 %.

Example 10

Methyl-3-oxopentanoate (26 wt. %) was fluorinated in HF using $F_2$/$O_2$/$N_2$ in accordance with the following comparative example.

mixture was then neutralized with $NaHCO_3$. The product was extracted with ether.

Analysis of the product by $_1H$ and $^{19}F$ NMR showed 100% conversion of methyl-3-oxopentanoate. The isolated product was 92% pure methyl-2-fluoro-3-oxopentanoate. Radical fluorination impurities in the isolated product totaled 5%.

Example 11

Methyl-3-oxopentanoate (28 wt. %) was fluorinated in HF using $F_2$/$N_2$ in accordance with the following comparative example.

A 300 mL Parr reactor was charged with 59.5 g (458 mmol) methyl-3-oxopentanoate. The reactor was externally cooled to about −35° C. and 155 mL anhydrous HF were condensed under static vacuum. This corresponds to a substrate loading of 28 wt. %. About 1.06 equivalents (484 mmol) of $F_2$ were sparged as a 10% $F_2$/90% $N_2$ stream into the reactor at −30° C. at 800 mL/min, allowing the effluent to pass through a soda-lime scrubber. After addition of $F_2$, HF solvent was evacuated through a soda-lime scrubber. The reactor was then opened and 100 mL $H_2O$ were added. The mixture was then neutralized with $NaHCO_3$. The product was extracted with ether.

Analysis of the product by $_1H$ and $^{19}F$ NMR showed 99% conversion of methyl-3-ntanoate. The isolated product was 81% pure methyl-2-fluoro-3-oxopentanoate. Radical fluorination impurities in the isolated product totaled 15%.

The results from the foregoing examples are summarized in the following table:

TABLE

| Example | Substrate | Solvent | Electrophile | Equiv. | Loading (wt. %) | T (C.) | Conversion | Isolated putiry[a] | Radical fluorination |
|---|---|---|---|---|---|---|---|---|---|
| 1 | methyl-3-oxopentanoate | HF | BDM | 1 | 10 | −20 | 83% | 82% | <0.5% |
| 2 | methyl-3-oxopentanoate | 1:3 HF/MeOH | BDM | 0.9 | 20 | −25 | 80% | 72% | <5% |
| 3 | methyl-3-oxopentanoate | 1:6 HF/MeOH | BDM | 1.1 | 10 | −25 | 40% | 40% | <1% |
| 4 | methyl-3-oxopentanoate | HF | BDM | 1.1 | 80 | −20 | 100% | 95% | 4% |
| 5 | ethyl-4,4,4-trifluoroacetoacetate | neat | BDM | 1 | 100 | −10 | 75% | 62% | 12% |
| 6 | methyl-3-oxopentanoate | HF | BDM/$F_2$ | 0.7:0.6 | 80 | −25 | 100% | 68% | 30% |
| 7 | methyl-3-oxopentanoate | HF | BDM/$F_2$ | 0.6:0.5 | 50 | −25 | 95% | 91% | 3% |
| 8 | methyl-3-oxopentanoate | HF | BDM/$F_2$ | 0.6:0.5 | 85 | −25 | 91% | 81% | 7% |
| 9 | methyl-3-oxopentanoate | HF | $F_2$/air | 1.1 | 38 | −30 | 100% | 85% | 11% |
| 10 | methyl-3-oxopentanoate | HF | $F_2$/air | 1.04 | 26 | −30 | 100% | 92% | 5% |
| 11 | methyl-3-oxopentanoate | HF | $F_2$/$N_2$ | 1.06 | 28 | −30 | 99% | 81% | 14–15% |

[a]Unfluorinated starting material, α,α-difluorinated material, as well as radical fluorination products, are included as impurities in calculation of the isolated purity.

A 300 mL Parr reactor was charged with 55.1g (424 mmol) methyl-3-oxopentanoate. The reactor was externally cooled to about −35° C. and 150 mL anhydrous HF were condensed under static vacuum. This corresponds to a substrate loading of 26 wt. %. About 1.04 equivalents (442 mmol) of $F_2$ were sparged as a 10% $F_2$/10%$O_2$/80% $N_2$ stream into the reactor at −30° C. at 800 mL/min, allowing the effluent to pass through a soda-lime scrubber. After addition of $F_2$, HF solvent was evacuated through a soda-lime scrubber. The reactor was then opened and 100 mL $H_2O$ were added. The While the invention has been described in detail and with reference to specific examples thereof, it will be apparent to one skilled in the art that various changes and modifications can be made therein without departing from the spirit and scope thereof.

What is claimed is:

1. A process for providing an α-fluorinated-β-dicarbonyl, said process comprising electrophilically fluorinating a β-dicarbonyl with bis-fluoroxydifluoromethane in the presence of an acid to provide said α-fluorinated-β-dicarbonyl.

2. The process of claim 1, wherein said β-dicarbonyl is a diketone or ketoester.

3. The process of claim 1, wherein said β-dicarbonyl is methyl-3-oxopentanoate.

4. The process of claim 1, wherein said β-dicarbonyl is ethyl-4,4,4-trifluoroacetoacetate.

5. The process of claim 1, wherein said acid is at least one member selected from the group consisting of hydrofluoric acid, triflic acid, fluorosulfonic acid, sulfuric acid, formic acid, acetic acid, trifluoroacetic acid and boron trifluoride.

6. The process of claim 1, wherein said acid is HF.

7. The process of claim 1, wherein said bis-fluoroxydifluoromethane is reacted in a medium comprising 10–25 wt. % β-dicarbonyl and 90–75 wt. % acid.

8. The process of claim 1, wherein said bis-fluoroxydifluoromethane is reacted in a medium comprising 10–25 wt. % β-dicarbonyl and 90–75 wt. % of a mixture comprising acid and methanol in an acid/methanol ratio greater than 1/6.

9. The process of claim 1, wherein said bis-fluoroxydifluoromethane is reacted in a medium comprising 80–90 wt. % β-dicarbonyl and 20–10 wt. % acid.

10. The process of claim 9, wherein a yield of α-monofluorinated-β-dicarbonyl is at least 95% of a theoretical yield.

11. The process of claim 1, wherein a yield of α-monofluorinated-β-dicarbonyl is at least 95% of a theoretical yield.

12. The process of claim 1, wherein at least 1 equivalent of bis-fluoroxydifluoromethane is added per equivalent of β-dicarbonyl.

13. The process of claim 12, wherein less than 0.5% of products of said process are radical impurities.

14. The process of claim 1, wherein not more than 4% of products of said process are radical impurities.

15. The process of claim 1, wherein said β-dicarbonyl compound is a methyl-3-oxopentanoate and said α-fluorinated-β-dicarbonyl compound is a methyl-2-fluoro-3-oxopentanoate.

16. The process of claim 1, wherein said α-fluorinated-β-dicarbonyl is an α-monofluorinated-β-dicarbonyl.

17. The process of claim 3, wherein said α-fluorinated-β-dicarbonyl is methyl-2-fluoro-3-oxopentanoate.

18. The process of claim 4, wherein said α-fluorinated-β-dicarbonyl is ethyl-2,4,4,4-tetrafluoroacetoacetate.

19. The process of claim 1, wherein said β-dicarbonyl is electrophilically fluorinated with a mixture of bis-fluoroxydifluoromethane and fluorine.

* * * * *